United States Patent [19]

Scherkenbeck et al.

[11] Patent Number: 5,304,568
[45] Date of Patent: Apr. 19, 1994

[54] ETHYL-TRIAZOLYL DERIVATIVES

[75] Inventors: Jürgen Scherkenbeck, Leverkusen; Michael Lindemann, Hamm/Sieg; Stefan Dutzmann, Hilden; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 103,872

[22] Filed: Aug. 6, 1993

Related U.S. Application Data

[62] Division of Ser. No. 42,339, Apr. 2, 1993, Pat. No. 5,266,584.

Foreign Application Priority Data

Apr. 14, 1992 [DE] Fed. Rep. of Germany ....... 4212424
Dec. 4, 1992 [DE] Fed. Rep. of Germany ....... 4240867

[51] Int. Cl.$^5$ ................ A01N 43/653; C07D 249/08
[52] U.S. Cl. ........................ 514/383; 514/184; 548/101; 548/262.2; 548/267.2; 548/267.4; 548/267.8; 548/268.6
[58] Field of Search ............... 514/383, 184; 548/101, 548/262.2, 267.2, 267.4, 267.8, 268.6

Primary Examiner—Patricia L. Morris
Attorney, Agent, or Firm—Sprung Horn Kramer & Woods

[57] ABSTRACT

New ethyl-triazolyl derivatives of the formula

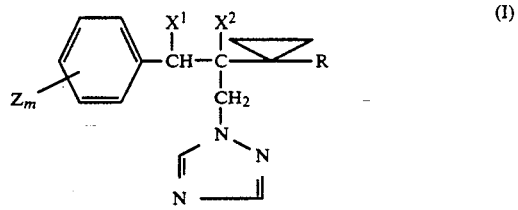

in which
R represents halogen,
$X^1$ represents fluorine, chlorine or bromine,
$X^2$ represents fluorine, chlorine or bromine,
Z represents halogen, alkyl having 1 to 4 carbon atoms, alkoxy having 1 to 4 carbon atoms, ethyl having 1 or 2 carbon atoms and 1 to 5 halogen atoms, halogenoalkoxy having 1 or 2 carbon atoms and 1 to 5 halogen atoms, phenyl, phenoxy, nitro or alkoximinoalkyl having 1 to 4 carbon atoms in the alkoxy moiety and 1 to 4 carbon atoms in the alkyl moiety and
m represents the numbers 0, 1, 2 or 3, and addition products thereof with acids or metal salts are very effective for combating fungi.

Novel ethyl-triazolyl derivatives of the formula

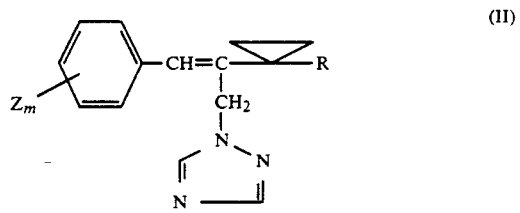

in which
R, Z and m have the abovementioned meanings, and addition products thereof with acids or metal salts are very effective for combating fungi.

The ethyl-triazolyl derivatives of the formula (II) are also valuable intermediates for the synthesis of ethyl-triazolyl derivatives of the formula (I).

8 Claims, No Drawings

ETHYL-TRIAZOLYL DERIVATIVES

This is a division of application Ser. No. 08/042,339, filed Apr. 2, 1993, now U.S. Pat. No. 5,266,589.

The present invention relates to new ethyl-triazolyl derivatives, to a process for their preparation, and to their use as fungicides.

It has already been disclosed that certain halogenoalkyltriazolyl derivatives have fungicidal properties (compare EP-OS (European Published Specification) 0,097,425). For example, 4-(2,4-dichloro-phenyl)-1,2-dibromo-4-hydroxy-5-(1,2,4-triazol-1-yl)-pent-1-ene and 4-(2,4-dichlorophenyl)-1,2-dichloro-4-hydroxy-5-(1,2,4-triazol-1-yl)pent-1-ene can be employed for combating fungi. The action of these substances is good, but occasionally leaves something to be desired when application rates are low.

New ethyl-triazolyl derivatives of the formula

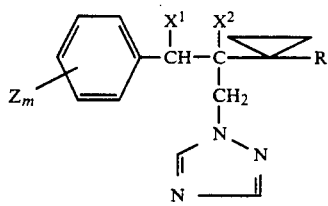

(I)

in which
R represents halogen,
X¹ represents fluorine, chlorine or bromine,
X² represents fluorine, chlorine or bromine,
Z represents halogen, alkyl having 1 to 4 carbon atoms, alkoxy having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, phenyl, phenoxy, nitro or alkoximinoalkyl having 1 to 4 carbon atoms in the alkoxy moiety and 1 to 4 carbon atoms in the alkyl moiety and
m represents the numbers 0, 1, 2 or 3,
and their acid addition salts and metal salt complexes have now been found.

The compounds of the formula (I) contain at least two asymmetrically substituted carbon atoms and can therefore be obtained in optical isomer form. The present invention relates to the isomer mixtures as well as to the individual isomers.

Furthermore, it has been found that ethyl-triazolyl derivatives of the formula (I) and their acid addition salts and metal salt complexes are obtained when ethyl-triazolyl derivatives of the formula

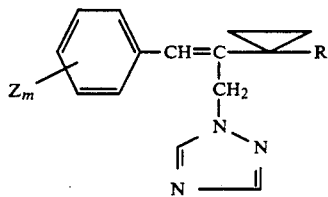

(II)

in which
R, Z and m have the abovementioned meanings are reacted with halogens of the formula $$X^1-X^2 \quad (III)$$

in which
X¹ and X² have the abovementioned meanings, or with compounds which generate halogens of the formula (III), in the presence of a diluent and, if appropriate, with irradiation, and, if appropriate, an acid or a metal salt is added on to the resulting compounds of the formula (I).

Moreover, new ethyl-triazolyl derivatives of the formula

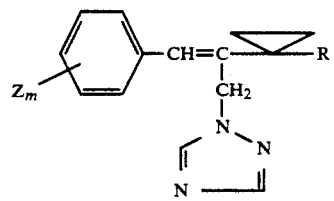

(II)

in which
R represents halogen,
Z represents halogen, alkyl having 1 to 4 carbon atoms, alkoxy having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, phenyl, phenoxy, nitro or alkoximinoalkyl having 1 to 4 carbon atoms in the alkoxy moiety and 1 to 4 carbon atoms in the alkyl moiety and
m represents the numbers 0, 1, 2 or 3,
and their acid addition salts and metal salt complexes have been found.

Depending on the position of the substituents at the double bond, the compounds of the formula (II) can exist in the form of geometric isomers. If the phenyl radical and the cyclopropyl radical are located on opposite sides of the double bond, the compounds are E isomers. If the phenyl radical and the cyclopropyl radical are on the same side of the double bond, the compounds are Z isomers. The present invention relates to the isomer mixtures as well as to the individual isomers.

Moreover, it has been found that the ethyl-triazolyl derivatives of the formula (II) and their acid addition salts and metal salt complexes are obtained when azolylmethyl ketones of the formula

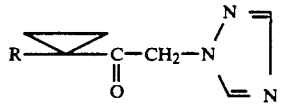

(IV)

in which
R has the abovementioned meaning are reacted with phosphonium salts of the formula

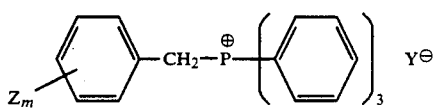

(V)

in which
Z and m have the abovementioned meanings and
Y represents chlorine or bromine, in the presence of a base and in the presence of a diluent, and, if appropriate, an acid or a metal salt is added on to the resulting compounds of the formula (II).

Finally, it has been found that the new ethyl-triazolyl derivatives of the formulae (I) and (II) and their acid addition salts and metal salt complexes have very good fungicidal properties.

Surprisingly, the substances according to the invention show a considerably better fungicidal activity than the previously known compounds which have the same direction of action and the most similar constitution.

Formulae (I) and (II) provide a general definition of the ethyl-triazolyl derivatives according to the invention.

R preferably represents fluorine, chlorine or bromine.

$X^1$ preferably represents fluorine, chlorine or bromine.

$X^2$ preferably represents fluorine, chlorine or bromine.

Z preferably represents fluorine, chlorine, bromine, methyl, ethyl, n-propyl, isopropyl, tert.-butyl, methoxy, ethoxy, halogenoalkyl having 1 or 2 carbon atoms and 1 to 3 fluorine, chlorine and/or bromine atoms, halogenoalkoxy having 1 or 2 carbon atoms and 1 to 3 fluorine, chlorine and/or bromine atoms, phenyl, phenoxy, nitro or alkoximinoalkyl having 1 or 2 carbon atoms in the alkoxy group and 1 or 2 carbon atoms in the alkyl group.

m preferably represents the numbers 0, 1 or 2.

R particularly preferably represents fluorine or chlorine.

$X^1$ particularly preferably represents fluorine, chlorine or bromine.

$X^2$ particularly preferably represents fluorine, chlorine or bromine.

Z particularly preferably represents fluorine, chlorine, bromine, methyl, ethyl, n-propyl, isopropyl, tert.-butyl, methoxy, ethoxy, trifluoromethyl, trichloromethyl, trifluoromethoxy, difluorochloromethoxy, phenyl, phenoxy, nitro, methoximinomethyl, ethoximinomethyl or 1-methoximinoethyl.

m particularly preferably represents the numbers 0, 1 or 2.

Other preferred substances according to the invention are addition products of acids and those ethyl-triazolyl derivatives of the formula (I) in which R, $X^1$, $X^2$, Z and m have the meanings mentioned above as being preferred or those ethyl-triazolyl derivatives of the formula (II) in which R, Z and m have the meanings mentioned above as being preferred.

The acids which can be added on preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, as well as sulphonic acids such as, for example, p-toluenesulphonic acid, 1,5-naphthalenedisulphonic acid or camphorsulphonic acid, and furthermore also saccharine and thiosaccharine.

Other preferred substances according to the invention are addition products of salts of metals of main group II to IV and sub-group I and II as well as IV to VIII of the Periodic System of the Elements and ethyl-triazolyl derivatives of the formula (I) in which R, $X^1$, $X^2$, Z and m have the meanings mentioned above as being preferred or those ethyl-triazolyl derivatives of the formula (II) in which R, Z and m have the meanings mentioned above as being preferred.

Salts of copper, zinc, manganese, magnesium, tin, iron and of nickel are particularly preferred in this context. Suitable anions of these salts are those which are derived from those acids which give physiologically acceptable addition products. Acids of this type which are particularly preferred in this context are the hydrohalic acids such as, for example, hydrochloric acid and hydrobromic acid, furthermore phosphoric acid, nitric acid and sulphuric acid.

Examples of substances according to the invention which may be mentioned are the ethyl-triazolyl derivatives listed in Tables 1 and 2 which follow.

TABLE 1

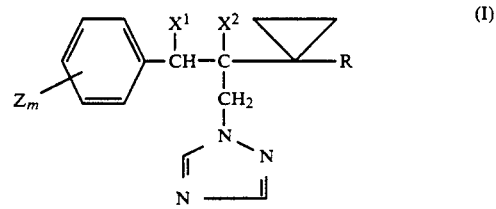

(I)

| $Z_m$ | $X^1$ | $X^2$ | R |
|---|---|---|---|
| 2,4-Cl$_2$ | Br | Br | Cl |
| 2-Cl | Br | Br | F |
| 4-CH$_3$ | Cl | Cl | Cl |
| 4-CF$_3$ | Cl | Cl | Cl |
| 4-OCH$_3$ | Cl | Cl | Cl |
| 4-⟨phenyl⟩ | Cl | Cl | Cl |
| 4-O-⟨phenyl⟩ | Cl | Cl | Cl |
| 4-CH=N—OCH$_3$ | Cl | Cl | Cl |
| 2-F | Cl | Cl | F |
| 4-Cl | Br | Br | Cl |
| 3-Cl | Cl | Cl | F |
| 2,6-Cl$_2$ | Cl | Cl | Cl |
| 2,6-Cl$_2$ | Cl | Cl | F |
| 3-F | Cl | Cl | F |
| 4-F | Cl | Cl | F |
| 2,4-F$_2$ | Cl | Cl | F |
| 2,6-F$_2$ | Cl | Cl | F |
| 2-Br | Cl | Cl | F |
| 3-Br | Cl | Cl | Cl |
| 3-Br | Cl | Cl | F |
| 4-Br | Cl | Cl | Cl |
| 4-Br | Cl | Cl | F |
| 4-NO$_2$ | Cl | Cl | Cl |
| 4-OCF$_3$ | Cl | Cl | Cl |

TABLE 2

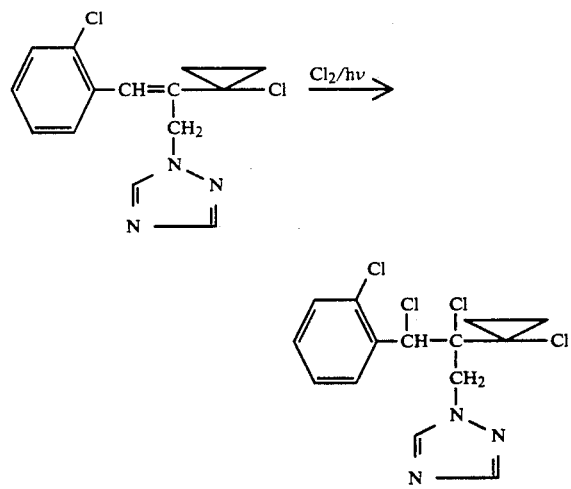

| Zm | R |
|---|---|
| 4- (phenyl) | Cl |
| 4- (phenyl) | F |
| 4-O-(phenyl) | Cl |
| 4-O-(phenyl) | F |
| 4-CH=N—OCH₃ | Cl |
| 4-CH=N—OCH₃ | F |
| 4-OCF₃ | Cl |
| 4-OCF₃ | F |

If 2-(1-chlorocyclopropyl)-1-(1,2,4-triazol-1-yl)-3-(2-chlorophenyl)-2-propene is used as starting material and chlorine gas as reactant, the course of the process according to the invention for the preparation of compounds of the formula (I) can be illustrated by the following equation:

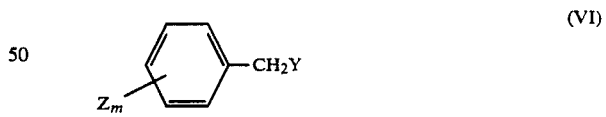

If 1-chloro-cyclopropyl (1,2,4-triazol-1-yl)-methyl ketone and 2-chlorobenzyl-triphenylphosphonium chloride are used as starting materials and potassium tert.-butylate is used as base, the course of the process according to the invention for the preparation of compounds of the formula (II) can be illustrated by the following equation:

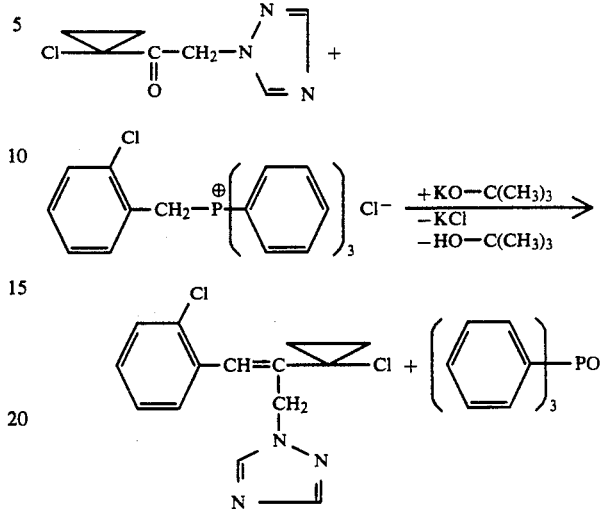

As already mentioned above, the ethyl-triazolyl derivatives of the formula (II) which are required as starting materials for carrying out the process according to the invention for the preparation of compounds of the formula (I) are new substances according to the invention which can be prepared by the respective above-mentioned process.

The azolylmethyl ketones of the formula (IV) required as starting materials for carrying out the process according to the invention for the preparation of compounds of the formula (II) are known or can be prepared in a simple manner by processes known in principle (cf. DE-OS (German Published Specification) 2,431,407 and EP-OS (European Published Specification) 0,353,558).

The phosphonium salts of the formula (V) which are required as reactants in the process according to the invention for the preparation of compounds of the formula (II) are also known or can be prepared by methods known in principle. For example, phosphonium salts of the formula (V) are obtained by reacting benzyl halides of the formula $$\underset{Z_m}{\underset{|}{\text{(benzene ring)}}}-CH_2Y \qquad (VI)$$

in which

Y, Z and m have the abovementioned meanings, with triphenylphosphine at temperatures between 110° C. and 150° C., if appropriate in the presence of a diluent such as xylene or toluene.

Bases which are suitable for the preparation of ethyl-triazolyl derivatives of the formula (II) by the above process are all strong acid acceptors which are customary for such Wittig reactions. Alcoholates such as potassium tert.-butylate, and hydrides such as sodium hydride, can preferably be used.

Diluents which are suitable in the above process for the preparation of ethyl-triazolyl derivatives of the formula (II) are all inert organic solvents which are customary for such reactions. Ethers such as diethyl ether, dioxane or tetrahydrofuran, and furthermore strongly polar solvents such as dimethyl sulphoxide, can preferably be used.

When carrying out the above process for the preparation of ethyl-triazolyl derivatives of the formula (II), the reaction temperatures can be varied within a certain range. In general, the process is carried out at temperatures between $-10°$ C. and $+80°$ C., preferably between $-5°$ C. and $+60°$ C.

The above process for the preparation of ethyl-triazolyl derivatives of the formula (II) is generally carried out under atmospheric pressure. However, it is also possible to carry out the process under increased or reduced pressure.

When carrying out the above process for the preparation of ethyl-triazolyl derivatives of the formula (II), 1 to 1.2 moles of phosphonium salt of the formula (V) and 1.2 to 2 moles of base are generally employed per mole of azolylmethyl ketone of the formula (IV). Working-up is carried out by customary methods. In general, a procedure is followed in which the reaction mixture is poured into water or a saturated aqueous ammonium chloride solution, the mixture is extracted with an organic solvent which is sparingly miscible with water, and the combined organic phases are dried and concentrated under reduced pressure. If desired, the product which remains can be purified further by customary methods.

When carrying out the process for the preparation of ethyl-triazolyl derivatives of the formula (II), the compounds are generally obtained in the form of E/Z isomer mixtures. The isomer mixtures can be separated by customary methods to give the individual geometric isomers. To isolate individual isomers, a procedure is generally followed in which the isomer mixtures are subjected to separation by column chromatography.

Halogens of the formula (III) which are suitable for carrying out the process according to the invention for the preparation of compounds of the formula (I) are fluorine, chlorine and bromine, furthermore mixed halogens, such as chlorine monofluoride, bromine monofluoride or bromine monochloride (cf. Methodicum Chimicum, F. Korte, Vol. 7, p. 842 (1976)).

The following can be used as compounds which generate halogens of the formula (III): sulphuryl chloride, N-bromo-succinimide with hydrochloric acid, N-chloro-succinimide with hydrobromic acid or N-chlorosuccinimide with hydrofluoric acid and pyridine (cf. Synthesis 1973, 780).

The addition of halogens on to ethyl-triazolyl derivatives of the formula (II) can be favoured by irradiation with light, by the action of heat by free-radical-forming substances such as organic peroxides, by surface-active substances such as active carbon, or metal salt such as copper(II) chloride or iron(III) chloride.

Diluents which can be employed for carrying out the process according to the invention for the preparation of compounds of the formula (I) are all inert solvents which are customary for such reactions. Halogenated aliphatic hydrocarbons such as methylene chloride, chloroform and carbon tetrachloride, or else phosphorus oxychloride, can preferably be used.

When carrying out the process according to the invention for the preparation of compounds of the formula (I), the temperatures can be varied within a certain range. In general, the process is carried out at temperatures between $-10°$ C. and $+120°$ C., preferably between $-5°$ C. and $80°$ C.

The process according to the invention for the preparation of compounds of the formula (I) is generally carried out under atmospheric pressure However, it can also be carried out under increased pressure.

When carrying out the process according to the invention for the preparation of compounds of the formula (I), an equivalent amount, or else an excess, of halogen of the formula (III) or of compounds which generate halogens of the formula (III) is generally employed per mole of ethyl-triazolyl derivative of the formula (II). Working-up is carried out by customary methods. In general, a procedure is followed in which the reaction mixture is washed with water, and the organic phase is dried and concentrated. However, it is also possible to concentrate the reaction mixture directly, after the reaction has ended, by stripping off the volatile components under reduced pressure. If desired, the substances obtained can be purified further by customary methods.

The ethyl-triazolyl derivatives of the formulae (I) and (II) according to the invention can be converted into acid addition salts or metal salt complexes.

Suitable acids for the preparation of acid addition salts of the compounds of the formulae (I) and (II) are preferably those which have already been mentioned in connection with the description of the acid addition salts according to the invention as being preferred.

The acid addition salts of the compounds of the formulae (I) and (II) can be obtained in a simple manner by customary salt formation methods, for example by dissolving a compound of the formula (I) or (II) in a suitable inert solvent and adding the acid, for example hydrochloricacid, and isolated in a customary manner, for example by filtration, and, if appropriate, purified by washing with an inert organic solvent.

Suitable salts for the preparation of metal salt complexes of the compounds of the formulae (I) and (II) are preferably those salts of metals which have already been mentioned in connection with the description of the metal salt complexes according to the invention as being preferred metal salts.

The metal salt complexes of the compounds of the formulae (I) and (II) can be obtained in a simple manner by customary processes, for example by dissolving the metal salt in alcohol, for example ethanol, and adding the solution to compounds of the formulae (I) or (II). Metal salt complexes can be isolated in a known manner, for example by filtration, and, if appropriate, purified by recrystallisation.

The active compounds according to the invention show a powerful microbicidal action and can be employed as fungicides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;* Erwinia species, such as *Erwinia amylovora;*
Pythium species, such as *Pythium ultimum;* Phytophthora species, such as *Phytophthora infestans;*
Pseudoperonospora species, such as *Pseudoperonospora humuli* or *Pseudoperonospora cubensis;* Plasmopara species, such as *Plasmopara viticola;* Peronospora species, such as *Peronospora pisi* or *P. brassicae;*

Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium);

Cochliobolus species, such as *Cochliobolus sativus* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;*

Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and *Pellicularia sasakii* on rice and for combating cereal diseases such as *Leptosphaeria nodorum, Cochliobolus sativus, Pyrenophora teres, Pseudocercosporella herpotrichoides,* Erysiphe and Fusarium species. Moreover, the substances according to the invention have a very good action against Venturia, Sphaerotheca and Botrytis. They have also have a broad in-vitro action.

The substances according to the invention can be converted into the customary formulations, such as solutions, emulsions, suspensions, powders, foams, pastes, qranules, aerosols, very fine capsules in polymeric substances and in coating compositions for seed, as well as ULV formulations. These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations in a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When employing the substances according to the invention, the application rate can be varied within a substantial range, depending on the way in which the substances are applied. For example, in the treatment of parts of plants, the active compound concentrations in the use forms are generally between 1 and 0.0001% by weight, preferably between 0.5 and 0.001%. In the treatment of seed, amounts of active compound of 0.001 to 50 g, preferably 0.01 to 10 g, are generally required per kilogram of seed. For the treatment of the soil, active compound concentrations of 0.00001 to 0.1% by weight, preferably 0.0001 to 0.02%, are required at the place of action.

The preparation and the use of the substances according to the invention can be seen from the examples which follow.

PREPARATION EXAMPLES

Example 1

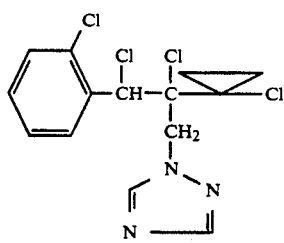
(I-1)

At 5° C. to 10° C., a stream of chlorine gas is passed for 2 hours into a solution of 20 g (68 mmol) of 2-(1-chlorocyclopropyl)-1-(1,2,4-triazol-1-yl)-3-(2-chlorophenyl)-2-propene (E/Z isomer mixture) in 150 ml of dichloromethane while exposing to UV light. Stirring of the reaction mixture is then continued for one hour at 5° C. to 10° C., and the mixture is subsequently washed with ice-water. The organic phase is dried over sodium sulphate and concentrated by stripping off the volatile components under reduced pressure. The residue which remains is chromatographed on silica gel using a mixture of cyclohexane:ethyl acetate 5:1 as eluent. In this manner, 9.4 g (38% of theory) of 2-(1-chlorocyclopropyl)-3-(2-chlorophenyl)-2,3-dichloro-1-(1,2,4-triazol-1-yl)-propane (diastereomer mixture) is obtained in the form of a solid.

1H NMR (200 MHz, CDCl$_3$/TMS): δ=0.3–1.3 (m,4H); 3.9 (d,1H); 5.25 (d,1H); 6.65 (s,1H); 7.2–7.4 (m,4H); 7.93 (s,1H); 8.22 (s,1H).

PREPARATION OF THE STARTING MATERIAL

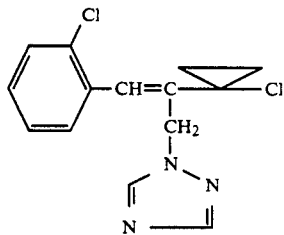
(II-1)

36.6 g (326 mmol) of potassium tert.-butylate are added at 0° C. with stirring, to a solution of 115 g (271 mmol) of 2-chlorobenzyl-triphenylphosphonium chloride in 600 ml of tetrahydrofuran. After the addition has ended, stirring is continued for one hour at 40° C. A solution of 50.4 g (271 mmol) of 1-chlorocyclopropyl-(1,2,4-triazol-1-yl)-methyl ketone in 300 ml of tetrahydrofuran is subsequently added dropwise at 30° C. with stirring. The reaction mixture is stirred for 16 hours at room temperature and then poured into saturated, aqueous ammonium chloride solution. The phases are separated, the aqueous phase is extracted several times using ethyl acetate, and the combined organic phases are dried over sodium sulphate and concentrated by stripping off the solvent under reduced pressure. The residue which remains is chromatographed on silica gel using a mixture of cyclchexane:ethyl acetate=2:1 as eluent. In this manner, 61.5 g (77% of theory) of 2-(1-chlorocyclopropyl)-1-(1,2,4-triazol-1-yl)-3-(2-chlorophenyl)-2-propene (E/Z isomer mixture) are obtained in the form of a solid of melting point 82°–85° C.

Example 2

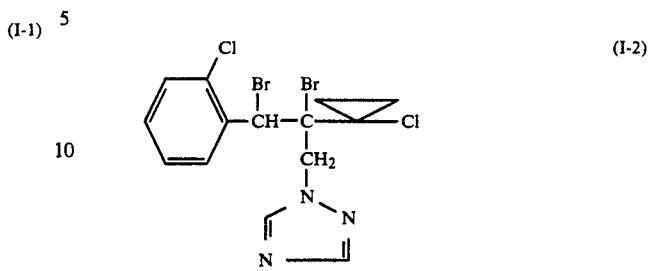
(I-2)

2.61 g (16.3 mmol) of bromine are added dropwise to solution of 4 g (13.6 mmol) of 2-(1-chlorocyclopropyl)-1-(1,2,4-triazol-1-yl)-3-(2-chlorophenyl)-2-propene (E/Z isomer mixture) in 50 ml of dichloromethane under reflux conditions and exposure to UV light. After the addition has ended, refluxing is continued for 6 hours under the exposure of UV light. 0.9 ml of bromine are subsequently added, and refluxing under exposure to UV light is continued for a further 16 hours. The reaction mixture is then cooled to room temperature and concentrated by stripping off the volatile components under reduced pressure. The residue which remains is chromatographed on silica gel using a mixture of cyclohexane:ethyl acetate=5:1 as eluent. In this manner, 0.97 g (16% of theory) of 2-(1-chloro-cyclopropyl)-3-(2-chlorophenyl)-2,3-dibromo-1-(1,2,4-triazol-1-yl)-propane (diastereomer mixture) in the form of a solid.

1H NMR (200 MHz, CDCl$_3$/TMS) 0.6–1.2 (m,4H); 4.0 (d,1H); 5.15 (d,1H); 6.63 (s,1H); 7.2–7.4 (m,4H); 7.95 (s,1H); 8.15 (s,1H).

The ethyl-triazolyl derivatives of the formula (I) which are listed in Table 3 which follows are also prepared by the abovementioned methods.

TABLE 3

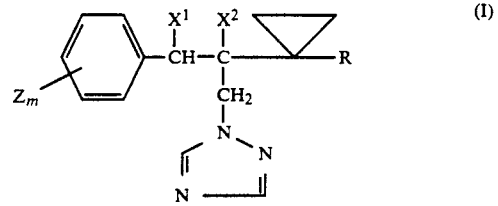
(I)

| Example | Comp. | $Z_m$ | $X^1$ | $X^2$ | R | Physical Constant |
|---|---|---|---|---|---|---|
| 3 | I-3 | 2,4-Cl$_2$ | Cl | Cl | Cl | diastereomer mixture |
| 4 | I-4 | 3,4-Cl$_2$ | Cl | Cl | Cl | diastereomer mixture |
| 5 | I-5 | 2,4-F$_2$ | Cl | Cl | Cl | diastereomer mixture |
| 6 | I-6 | 2-F | Cl | Cl | Cl | diastereomer mixture |
| 7 | I-7 | 2,3-Cl$_2$ | Cl | Cl | Cl | diastereomer mixture |
| 8 | I-8 | 3-Cl | Cl | Cl | Cl | diastereomer mixture |
| 9 | I-9 | 4-F | Cl | Cl | Cl | diastereomer mixture m.p. 121° C. |
| 10 | I-10 | 2-Br | Cl | Cl | Cl | diastereomer mixture |
| 11 | I-11 | 4-Cl | Cl | Cl | Cl | diastereomer mixture |
| 12 | I-12 | 3-F | Cl | Cl | Cl | diastereomer mixture |
| 13 | I-13 | 2,6-F$_2$ | Cl | Cl | Cl | diastereomer mixture m.p. 76° C. |
| 14 | I-14 | 4-Cl | Cl | Cl | F | diastereomer mixture |
| 15 | I-15 | 2,4-Cl$_2$ | Cl | Cl | F | diastereomer mixture |
| 16 | I-16 | 2-Cl | Cl | Cl | F | diastereomer mixture |
| 17 | I-17 | 4-NO$_2$ | Cl | Cl | F | diastereomer mixture |

The following ¹H NMR signals (CdCl₃, TMS, 200 MHz, δ values) are used for characterising compounds of Table 3:

| Example 3: | 0.2–0.8 (m, 2H), 1.1–1.6 (m, 2H), 3.8–4.1 (m, 1H), 5.1–5.4 (m, 1H), 6.6 (s, 1H), 7.3–7.6 (m, 3H), 8.0 and 8.1 (s, tog. 1H), 8.05 and 8.15 (s, tog. 1H) |
|---|---|
| Example 4: | 0.3–0.5 (m, 1H), 0.65–0.85 (m, 1H), 1.1–1.2 (m, 1H), 1.4–1.6 (m, 1H), 4.0 (d, 1H), 4.9 (d, 1H), 5.8 (s, 1H), 7.5 (m, 2H), 7.75 (d, 1H), 7.95 (s, 1H), 8.2 (s, 1H) |
| Example 5: | 0.1–0.8 (m, 2H), 1.1–1.6 (m, 2H), 3.9 (d), 4.9 (d), 5.1 (d, tog. 2H), 5.8 (s, 1H), 6.95–7.2 (m, 2H), 7.5–7.7 (m, 1H), 8.1 (s, 1H), 8.4 (s, 1H) |
| Example 6: | 0.2–0.8 (m, 2H), 1.1–1.6 (m, 2H), 4.0 (d), 5.1 (d), 5.15 (m, tog. 2H), 6.2 and 6.3 (s, tog. 1H), 7.0–7.5 (m, 3H), 7.8–8.0 (m, 1H), 7.95 and 8.0 (s, tog. 1H), 8.25 and 8.45 (s, tog. 1H) |
| Example 7: | 0.3–0.8 (m, 2H), 1.2–1.6 (m, 2H), 3.7–4.0 (m, 1H), 5.0–5.3 (m, 1H), 6.35 and 6.7 (s, tog. 1H), 7.1–7.6 (m, 2H), 7.9–8.1 (m, 1H), 7.95 and 8.05 (s, tog. 1H), 8.25 and 8.4 (s, tog. 1H) |
| Example 8: | 0.2–0.8 (m, 2H), 1.1–1.6 (m, 2H), 3.95 (d, 1H), 4.9 (d, 1H), 5.75 and 5.85 (s, tog. 1H), 7.2–7.7 (m, 4H), 7.95 and 8.0 (s, tog. 1H), 8.2 and 8.3 (s, tog. 1H) |
| Example 9: | 0.1–0.8 (m, 4H), 5.2 (d, 2H), 5.8 (s, 1H), 7.0–7.2 (m, 2H), 7.6–7.8 (m, 2H), 8.05 (s, 1H), 8.4 (s, 1H) |
| Example 10: | 0.1–1.5 (m, 4H), 5.0 (m, 2H), 5.8 (m, 1H), 7.0–7.6 (m, 4H), 8.0 and 8.1 (s, tog. 1H), 8.5 and 8.7 (s, tog. 1H) |
| Example 11: | 0.3–0.5 (m, 1H), 0.6–0.8 (m, 1H), 1.1–1.2 (m, 1H), 1.4–1.6 (m, 1H), 3.95 (d, 1H), 4.9 (d, 1H), 5.85 (s, 1H), 7.4 (d, 2H), 7.6 (d, 2H), 7.95 (s, 1H), 8.25 (s, 1H) |
| Example 12: | 0.2–0.8 (m, 2H), 1.1–1.6 (m, 2H), 3.95 (d), 4.9 (d), 5.1 (d, tog. 2H), 5.75 and 5.85 (s, tog. 1H), 7.0–7.6 (m, 4H), 7.95 and 8.0 (s, tog. 1H, 8.25–8.3 (s, 1H) |
| Example 13: | 0.3–0.7 (m, 2H), 1.1–1.6 (m, 2H), 4.25 (d, 1H), 5.15 (d, 1H), 6.2 (s, 1H), 6.9–7.5 (m, 3H) 8.0 (s, 1H), 8.3 (s, 1H) |
| Example 14: | 0.2–0.5 (m, 1H), 0.6–0.9 (m, 1H), 1.0–1.4 (m, 2H), 4.2 (d, 1H), 4.8 (d, 1H), 5.6 (s, 1H), 7.4 (d, 2H), 7.6 (d, 2H), 8.0 (s, 1H), 8.2 (s, 1H) |
| Example 15: | 0.1–0.4 (m, 1H), 0.6–0.9 (m, 1H), 1.0–1.4 (m, 2H), 4.05 (d, 1H), 5.1 (d, 1H), 6.3 (s, 1H), 7.4–7.6 (m, 2H), 7.9–8.1 (m, 1H), 8.0 (s, 1H), 8.2 (s, 1H) |
| Example 16: | 0.3–1.4 (m, 4H), 4.15 (d), 5.1 (d) and 5.2 (m, tog. 2H), 6.3 and 6.4 (s. tog. 1H), 7.2–7.4 (m, 4H), 8.1 (s) and 8.35 (s, tog. 1H), 8.3 and 8.6 (s, tog. 1H) |
| Example 17: | 0.2–0.7 (m, 2H), 1.2–1.6 (m, 2H), 4.0 (d), 5.0 (d), 5.2 (d, tog. 2H), 5.9 and 5.95 (s. tog. 1H), 7.6–8.4 (m, 6H) |

The ethyl-triazolyl derivatives of the formula (II) listed in Table 4 which follows are also prepared by the method indicated in Example 1.

TABLE 4

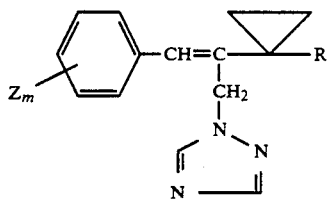

(II)

| Ex. No. | Comp. No. | $Z_m$ | R | Isomer | Physical Constant |
|---|---|---|---|---|---|
| 18 | II-2 | 2-Cl | Cl | Z | 0.4–0.5 (m, 2H), 1.0–1.1 (m, 2H), 5.2 (s, 2H), 6.6 (s, 1H), 7.25–7.4 (m, 3H), 7.7–7.8 (m, 1H), 8.0 (s, 1H), 8.3 (s, 1H)*⁾ |
| 19 | II-3 | 2-Cl | Cl | E | 0.7–0.8 (m, 2H), 1.0–1.1 (m, 2H), 5.15 (s, 2H), 6.9 (s, 1H), 7.25–7.35 (m, 2H), 7.4–7.5 (m, 1H), 7.7–7.8 (m, 1H), 8.0 (s, 1H), 8.3 (s, 1H)*⁾ |
| 20 | II-4 | 3-Cl | Cl | E/Z | 0.5–1.1 (m, 4H), 5.12 (s), 5.2 (s, tog. 2H), 6.4 (s), 6.85 (s, tog. 1H), 7.2–7.75 (m, 4H), 7.99 (s), 8.01 (s, tog. 1H), 8.29 (s), 8.31 (s, tog. 1H)*⁾ |
| 21 | II-5 | 4-Cl | Cl | E | 0.7–0.8 (m, 2H), 1.0–1.1 (m, 2H), 5.2 (s, 2H), 6.85 (s, 1H), 7.2–7.55 (m, 4H), 8.0 (s, 1H), 8.3 (s, 1H)*⁾ |
| 22 | II-6 | 2,4-Cl₂ | Cl | E | 0.7–0.8 (m, 2H), 1.0–1.1 (m, 2H), 5.1 (s, 2H), 6.8 (s, 1H), 7.2–7.5 (m, 2H), 7.8 (d, 1H), 8.0 (s, 1H), 8.28 (s, 1H)*⁾ |
| 23 | II-7 | 2,4-Cl₂ | Cl | Z | m.p. 106° C. |
| 24 | II-8 | 2,6-Cl₂ | Cl | E/Z | 0.8–1.1 (m, 4H), 4.95 (s, 2H), 6.6 (s, 1H), 7.1–7.4 (m, 3H), 7.9 (s, 1H), 8.15 (s, 1H)*⁾ |
| 25 | II-9 | 3,4-Cl₂ | Cl | E/Z | 0.5–1.2 (m, 4H), 5.1 (s), 5.15 (s, tog. 2H), 6.3 (s), 6.8 (s, tog. 1H), 7.2–7.7 (m, 3H), 7.97 (s), 8.0 (s, tog. 1H), 8.28 (s), 8.3 (s, tog. 1H)*⁾ |
| 26 | II-10 | 2,3-Cl₂ | Cl | E/Z | 0.5–1.2 (m, 4H), 5.1 (s), 5.2 (s, tog. 2H), 6.5 (s), 6.9 (s, tog. 1H), 7.1–7.8 (m, 3H), 8.0 (s), 8.03 (s, tog. 1H), 8.29 (s), 8.30 (s, tog. 1H)*⁾ |
| 27 | II-11 | 2-F | Cl | E/Z | 0.5–1.2 (m, 4H), 5.15 (s), 5.18 (s, tog. 2H), 6.6 (s), 6.88 (s. tog. 1H), 7.0–7.8 (m, 4H), 7.98 (s), 8.01 (s, tog. 1H), 8.2 (s), 8.3 (s, tog. 1H)*⁾ |
| 28 | II-12 | 3-F | Cl | E/Z | 0.5–1.2 (m, 4H), 5.1 (s), 5.2 (s, tog. 2H), 6.4 (s), 6.85 (s, tog. 1H), 7.0–7.7 (m, 4H), 7.98 (s), 8.01 (s, tog. 1H), 8.28 (s) 8.31 (s, tog. 1H)*⁾ |
| 29 | II-13 | 4-F | Cl | E/Z | 0.5–1.2 (m, 4H), 5.1 (s), 5.15 (s, tog. 2H), 6.5 (s), 6.9 (s, tog. 1H), 7.0–7.8 (m, 4H), 7.98 (s), 8.0 (s, tog. 1H), 8.29 (s), 8.32 (s, tog. 1H).*⁾ |
| 30 | II-14 | 2,6-F₂ | Cl | E/Z | 0.5–1.2 (m, 4H), 5.05 (s), 5.2 (s, tog. 2H), 6.25 (s), 6.55 (s, tog. 1H), 6.9–7.8 (m, 3H), 7.9 (s), 8.0 (s, tog. 1H), 8.27 (s) 8.31 (s, tog. 1H)*⁾ |
| 31 | II-15 | 2,4-F₂ | Cl | E/Z | m.p. 84° C. |

TABLE 4-continued (II)

Structure: Z_m-phenyl-CH=C(-R-cyclopropyl)(-CH2-triazole)

| Ex. No. | Comp. No. | $Z_m$ | R | Isomer | Physical Constant |
|---|---|---|---|---|---|
| 32 | II-16 | 2,4-F$_2$ | Cl | Z | 0.5–0.6 (m, 2H), 1.1–1.2 (m, 2H), 5.15 (s, 2H), 6.5 (s, 1H), 6.9–7.1 (m, 2H), 7.4–7.5 (m, 1H), 8.0 (s, 1H), 8.3 (s, 1H)*) |
| 33 | II-17 | 2,4-F$_2$ | Cl | E | 0.7–0.8 (m, 2H), 1.0–1.1 (m, 2H), 5.2 (s, 2H), 6.8 (s, 1H), 6.95–7.1 (m, 2H), 7.5–7.65 (m, 2H), 8.0 (s, 1H), 8.3 (s, 1H)*) |
| 34 | II-18 | 2-Br | Cl | E/Z | 0.5–1.1 (m, 4H), 5.1 (s), 5.2 (s, tog. 2H), 6.5 (s), 6.85 (s, tog. 1H), 7.1–7.8 (m, 4H), 7.98 (s), 8.03 (s, tog. 1H), 8.25 (s), 8.3 (s, tog. 1H)*) |
| 35 | II-19 | 3-Br | Cl | E/Z | 0.5–1.2 (m, 4H), 5.1 (s), 5.2 (s, tog. 2H), 6.6 (s), 6.85 (s, tog. 1H), 7.1–7.8 (m, 4H), 8.0 (s, 1H), 8.3 (s, 1H)*) |
| 36 | II-20 | 4-Br | Cl | E | m.p. 88° C. |
| 37 | II-21 | 4-Br | Cl | Z | m.p. 94° C. |
| 38 | II-22 | 4-NO$_2$ | Cl | E | m.p. 64° C. |
| 39 | II-23 | 4-CF$_3$ | Cl | Z | 0.4–0.5 (m, 2H), 1.05–1.15 (m, 2H), 5.15 (s, 2H), 6.45 (s, 1H), 7.4–7.8 (m, 4H), 8.0 (s, 1H), 8.3 (s, 1H)*) |
| 40 | II-24 | 4-OCH$_3$ | Cl | E | 0.7–0.8 (m, 2H), 1.0–1.2 (m, 2H), 3.85 (s, 3H), 5.25 (s, 2H), 6.85 (s, 1H), 6.95 (d, 2H), 7.5 (d, 2H), 8.0 (s, 1H), 8.3 (s, 1H)*) |
| 41 | II-25 | 4-OCH$_3$ | Cl | Z | 0.45–0.55 (m, 2H), 1.1–1.2 (m, 2H), 3.85 (s, 3H), 5.1 (s, 2H), 6.55 (s, 1H), 6.95 (d, 2H), 7.5 (d, 2H), 8.0 (s, 1H), 8.3 (s, 1H)*) |
| 42 | II-26 | 4-CH$_3$ | Cl | E | 0.7–0.8 (m, 2H), 1.0–1.1 (m, 2H), 2.35 (s, 3H), 5.2 (s, 2H), 6.9 (s, 1H), 7.2 (d, 2H), 7.4 (d, 2H), 8.0 (s, 1H), 8.3 (s, 1H)*) |
| 43 | II-27 | 4-CH$_3$ | Cl | Z | 0.45–0.55 (m, 2H), 1.05–1.15 (m, 2H), 2.35 (s, 3H), 5.1 (s, 2H), 6.5 (s, 1H), 7.15 (d, 2H), 7.4 (d, 2H), 8.0 (s, 1H), 8.3 (s, 1H)*) |
| 44 | II-28 | 2-Cl | F | E | 0.6–0.8 (m, 2H); 1.0–1.2 (m, 2H), 5.05 (s, 2H), 6.85 (d, 1H), 7.2–7.3 (m, 2H), 7.4–7.5 (m, 1H), 7.7–7.8 (m, 1H), 8.0 (s, 1H), 8.2 (s, 1H)*) |
| 45 | II-29 | 3-Cl | F | E | 0.6–0.8 (m, 2H), 1.0–1.2 (m, 2H), 5.1 (s, 2H), 6.8 (d, 1H), 7.2–7.6 (m, 4H), 8.0 (s, 1H), 8.2 (s, 1H)*) |
| 46 | II-30 | 3-Cl | F | Z | 0.2–0.4 (m, 2H), 1.0–1.2 (m, 2H), 5.1 (s, 2H), 6.6 (s, 1H), 7.2–7.6 (m, 4H), 8.0 (s, 1H), 8.2 (s, 1H)*) |
| 47 | II-31 | 4-Cl | F | E/Z | 0.2–1.2 (m, 4H), 5.1 (s), 5.5 (d, tog. 2H), 6.6 (d), 6.8 (d, tog. 1H), 7.3–7.8 (m, 4H), 8.0 (s), 8.02 (s, tog. 1H), 8.18 (s), 8.22 (s, tog. 1H)*) |
| 48 | II-32 | 3,4-Cl$_2$ | F | E | 0.5–0.7 (m, 2H), 1.0–1.2 (m, 2H), 5.1 (s, 2H), 6.75 (d, 1H), 7.4–7.7 (m, 3H), 8.0 (s, 1H), 8.2 (s, 1H)*) |
| 49 | II-33 | 3,4-Cl$_2$ | F | Z | 0.2–0.4 (m, 2H), 1.0–1.2 (m, 2H), 5.1 (s, 2H), 6.5 (d, 1H), 7.2–7.5 (m, 3H), 8.0 (s, 1H), 8.2 (s, 1H)*) |
| 50 | II-34 | 2,4-Cl$_2$ | F | E | 0.6–0.8 (m, 2H), 1.0–1.2 (m, 2H), 5.0 (s, 2H), 6.8 (d, 1H), 7.3 (dd, 1H), 7.45 (d, 1H), 7.8 (d, 1H), 8.0 (s, 1H), 8.2 (s, 1H)*) |
| 51 | II-35 | 2,3-Cl$_2$ | F | E | 0.6–0.8 (m, 2H), 1.0–1.2 (m, 2H), 5.05 (s, 2H), 6.8 (d, 1H), 7.1–7.8 (m, 3H), 7.95 (s, 1H), 8.15 (s, 1H)*) |
| 52 | II-36 | 2,3-Cl$_2$ | F | Z | 0.2–0.4 (m, 2H), 0.9–1.1 (m, 2H), 5.15 (s, 2H), 6.75 (s, 1H), 7.1–7.5 (m, 3H), 8.0 (s, 1H), 8.25 (s, 1H)*) |
| 53 | II-37 | 2-F | F | E | m.p. 81° C. |
| 54 | II-38 | 2-F | F | Z | 0.25–0.45 (m, 2H), 1.0–1.2 (m, 2H), 5.1 (s, 2H), 6.75 (s, 1H), 7.0–7.6 (m, 4H), 8.0 (s, 1H), 8.2 (s, 1H)*) |
| 55 | II-39 | 3-F | F | E | m.p. 55° C. |
| 56 | II-40 | 3-F | F | Z | 0.25–0.45 (m, 2H), 1.0–1.2 (m, 2H), 5.15 (s, 2H), 6.65 (s, 1H), 6.95–7.4 (m, 4H), 8.0 (s, 1H), 8.2 (s, 1H)*) |
| 57 | II-41 | 4-F | F | E | 0.55–0.75 (m, 2H), 0.95–1.15 (m, 2H), 5.1 (s, 2H), 6.8 (d, 1H), 7.0–7.2 (m, 2H), 7.5–7.65 (m, 2H), 8.0 (s, 1H), 8.2 (s, 1H)*) |
| 58 | II-42 | 4-F | F | Z | 0.2–0.4 (m, 2H), 1.0–1.2 (m, 2H), 5.1 (s, 2H), 6.65 (s, 1H), 7.0–7.2 (m, 2H), 7.5–7.65 (m, 2H), 8.0 (s, 1H), 8.2 (s, 1H)*) |
| 59 | II-43 | 4-Cl | Cl | Z | m.p. 86° C. |

The symbols in Table 4 represent:
E = E isomer
Z = Z isomer
E/Z = E/Z isomer mixture
*) $^1$H NMR signals CDCl$_3$, TMS, 200 MHz δ values In the use examples which follow, the compounds of the formulae listed below were employed as comparison substances.

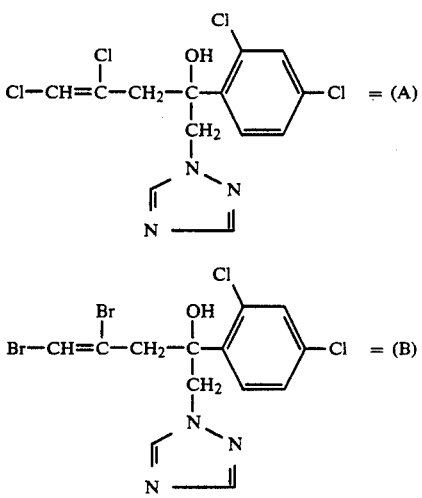

(Disclosed in EP-OS (European Published Specification) 0,097,425)

Example A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of approx. 20° C. and a relative atmospheric humidity of approx. 80% to favour the development of mildew pustules.

Evaluation is carried out 7 days after the inoculation.

In this test, the compound of the formula (I-1) according to the invention, at a concentration of 25 ppm in the spray liquor, shows a activity of over 90%, whereas the degree of effectiveness for the comparison substances (A) and (B) is between 0 and 25%.

Example B

Erysiphe test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. tritici.

The plants are placed in a greenhouse at a temperature of approx. 20° C. and a relative atmospheric humidity of approx. 80% to favour the development of mildew pustules.

Evaluation is carried out 7 days after the inoculation.

In this test, the compound of the formula (I-1) according to the invention, at a concentration of 25 ppm in the spray liquor, shows an activity of almost 80%, whereas the degree of effectiveness for the comparison substances (A) and (B is between 0 and 16%.

Example C

*Leptosphaeria nodorum* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of approx. 15° C. and a relative atmospheric humidity of approx. 80%.

The evaluation is carried out 10 days after the inoculation.

In this test, the compound of the formula (I-1) according to the invention, at a concentration of 250 ppm in the spray liquor, shows an activity of 100%, whereas the degree of effectiveness of the comparison substance (A) is 75%.

Example D

*Pseudocercosporella herpotrichoides* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the stem base of the plants is inoculated with spores of *Pseudocercosporella herpotrichoides*.

The plants are placed in a greenhouse at a temperature of approx. 10° C. and a relative atmospheric humidity of approx. 80%.

The evaluation is carried out 21 days after inoculation.

In this test, the compounds of the formulae (I-1) and (I-2) according to the invention, at a concentration of 250 ppm in the spray liquor, show an activity of 80 to 100%, whereas the degree of effectiveness for the comparison substances (A) and (B) is 50% and 0% respectively.

Example E

*Pyrenophora teres* test (barley)/protective
Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of approx. 20° C. and a relative atmospheric humidity of approx. 80%.

Evaluation is carried out 7 days after the inoculation.

In this test, the compound of the formula (I-1) according to the invention, at a concentration of 250 ppm in the spray liquor, shows a degree of effectiveness of 100%.

Example F

Uncinula test (vine)/protective
Solvent: 4.7 parts by weight of acetone
Emulsifier: 0.2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Uncinula necator*.

The plants are then placed in a greenhouse at 23° C. to 24° C. and at a relative atmospheric humidity of approx. 75%.

Evaluation is carried out 14 days after the inoculation.

In this test, the substances of the formulae (I-1) and (I-2) according to the invention, at a concentration of 10 ppm in the spray liquor, show a degree of effectiveness of 100%.

Example G

Erysiphe test (barley)/protective
Solvent: 14.8 parts by weight of dimethylformamide
Emulsifier: 1.2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the dosage rate indicated. After spray coating has dried on, the plants are dusted with spores of *Erysiphe graminis* f. sp. hordei.

The plants are placed in a greenhouse at a temperature of approx. 20° C. and a relative atmospheric humidity of approx. 80% to favour the development of mildew pustules.

Evaluation is carried out 7 days after the inoculation.

In this test, the compounds (II-1), (II-3) and (II-10) according to the invention show a degree of effectiveness of 100% at an application rate of 200 g/ha.

Example H

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After spray coating has dried on, the plants are dusted with spores of *Erysiphe graminis* f. sp. hordei.

The plants are placed in a greenhouse at a temperature of approx. 20° C. and a relative atmospheric humidity of approx. 80% to favour the development of mildew pustules.

Evaluation is carried out 7 days after the inoculation.

In this test, the compounds (I-1), (I-3), (I-11) and (II-22) according to the invention, at a concentration of 250 ppm in the spray liquor show a degree of effectiveness of 100%.

Example I

Podosphaera test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound until dripping wet. After the spray coating has dried on, the plants are inoculated by dusting with conidia of the apple scab positive organism (*Podosphaera leucotricha*).

The plants are then placed in a greenhouse at 23° C. and a relative atmospheric humidity of approx. 70%.

10 days after inoculation, the degree of effectiveness is determined and expressed in %. 0% means that no activity is observed (untreated control) and 100% means that the plants are free from disease.

In this test, the compounds (II-6), (II-33) and (II-36) according to the invention, at a concentration of 10 ppm in the spray liquor, show a degree of effectiveness of 100%.

It will be understood that the specification and examples are illustrative but not limitative of the present invention and that other embodiments within the spirit and scope of the invention will suggest themselves to those skilled in the art.

What is claimed is:

1. An ethyl-triazolyl derivative of the formula

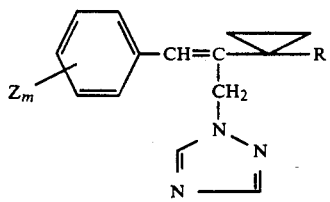

in which

R represents halogen,

Z represents halogen, alkyl having 1 to 4 carbon atoms, alkoxy having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, phenyl, phenoxy, nitro or alkoximinoalkyl having 1 to 4 carbon atoms in the alkoxy moiety and 1 to 4 carbon atoms in the alkyl moiety and m represents the numbers 0, 1, 2 or 3, or an addition product thereof with an acid or metal salt.

2. A compound according to claim 1, wherein

R represents fluorine, chlorine or bromine,

Z represents fluorine, chlorine, bromine, methyl, ethyl, n-propyl, isopropyl, tert.-butyl, methoxy, ethoxy, halogenoalkyl having 1 or 2 carbon atoms and 1 to 3 fluorine, chlorine and/or bromine atoms, halogenoalkoxy having 1 or 2 carbon atoms and 1 to 3 fluorine, chlorine and/or bromine atoms, phenyl, phenoxy, nitro or alkoximinoalkyl having 1 or 2 carbon atoms in the alkoxy group and 1 or 2 carbon atoms in the alkyl group and m represents the numbers 0, 1 or 2.

3. A compound according to claim 1, wherein such compound is the E/Z isomer mixture of 2-(1-chlorocyclopropyl)-1-(1,2,4-triazol-1-yl)-3-(2-chlorophenyl)-2-propene of the formula

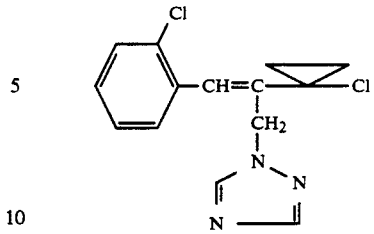

4. A compound according to claim 1, wherein such compound is the E-isomer of 2-(1-chlorocyclopropyl)-1-(1,2,4-triazol-1-yl)-3-(2-chlorophenyl)-2-propene of the formula

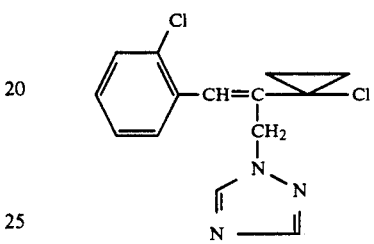

5. A compound according to claim 1, wherein such compound is the E/Z isomer mixture of 2-(1-chlorocyclopropyl)1-(1,2,4-triazol-1-yl)-3-(3,4-dichlorophenyl)-2-propene of the formula

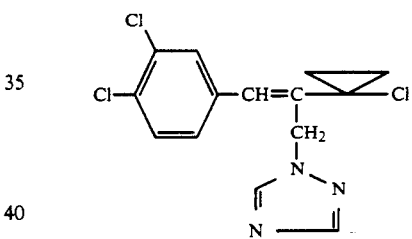

6. A fungicidal composition comprising a fungicidally effective amount of a compound or addition product according to claim 1 and an inert diluent.

7. A method of combating fungi, which method comprises applying to such fungi or to their habitat a fungicidally effective amount of a compound or addition product according to claim 1.

8. A method according to claim 7, wherein such compound is the E/Z isomer mixture of 2-(1-chlorocyclopropyl)-1-(1,2,4-triazol-1-yl)-3-(2-chlorophenyl)-2-propene, the E-isomer of 2-(1-chlorocyclopropyl)-1-(1,2,4-triazol-1-yl)-3-(2-chlorophenyl)-2-propene or the E/Z isomer mixture of 2-(1-chlorocyclopropyl)-1-(1,2,4-triazol-1-yl)-3-(3,4-dichloro-phenyl)-2-propene.

* * * * *